United States Patent
Youngblood (10) Patent No.: US 8,323,034 B1
(45) Date of Patent: Dec. 4, 2012

(54) VIRTUAL SURGICAL ASSISTANT

(76) Inventor: Terry Youngblood, Fort Worth, TX (US)

( * ) Notice: Subject to any disclaimer, the term of this patent is extended or adjusted under 35 U.S.C. 154(b) by 0 days.

(21) Appl. No.: 13/323,895

(22) Filed: Dec. 13, 2011

Related U.S. Application Data (63) Continuation-in-part of application No. 11/789,723, filed on Apr. 24, 2007, now Pat. No. 8,075,317.

(51) Int. Cl.
*G09B 25/00* (2006.01)
(52) U.S. Cl. .......... 434/428; 434/365
(58) Field of Classification Search .......... 434/365, 434/428
See application file for complete search history.

(56) References Cited

U.S. PATENT DOCUMENTS

| | | | |
|---|---|---|---|
| 4,360,345 | A | 11/1982 | Hon |
| 5,454,722 | A | 10/1995 | Holland et al. |
| 5,610,811 | A | 3/1997 | Honda |
| 5,991,728 | A | 11/1999 | DeBusk et al. |
| 6,158,437 | A | 12/2000 | Vagley |
| 2002/0048743 | A1 | 4/2002 | Schmieding et al. |
| 2002/0055918 | A1 | 5/2002 | Hlathein et al. |
| 2002/0095313 | A1 | 7/2002 | Haq |
| 2003/0216836 | A1 | 11/2003 | Treat et al. |
| 2004/0098286 | A1 | 5/2004 | Zimmerman et al. |
| 2004/0169673 | A1 | 9/2004 | Crampe et al. |
| 2005/0038442 | A1 | 2/2005 | Freeman |
| 2006/0059018 | A1 | 3/2006 | Shiobara et al. |

OTHER PUBLICATIONS

Office Action from counterpart U.S. Appl. No. 11/789,723, issued by the USPTO on Oct. 7, 2010.
Amendment dated Dec. 10, 2010 filed in response to the U.S. Office Action dated Oct. 7, 2010.
Examiner Interview Summary from counterpart U.S. Appl. No. 11/789,723, issued by the USPTO on Dec. 15, 2010.
Final Office Action from counterpart U.S. Appl. No. 11/789,723, issued by the USPTO on Mar. 17, 2011.
Amendment After Final dated May 16, 2011 filed in response to the Final Office Action dated Mar. 17, 2011.
Advisory Action from counterpart U.S. Appl. No. 11/789,723, issued by the USPTO on Jun. 1, 2011.
Notice of Allowance from counterpart U.S. Appl. No. 11/789,723, issued by the USPTO on Aug. 9, 2011.

*Primary Examiner* — Xuan Thai
*Assistant Examiner* — Evan Page
(74) *Attorney, Agent, or Firm* — James E. Walton; Richard G. Eldredge (57) ABSTRACT

A system and method for assisting a surgeon during a surgical procedure. The system including a portable device having a display and a database in data communication with the portable device. The database including a program having a first image of the first set of instructions to be conducted by a surgical scrub assisting the surgeon during the first step of the surgical procedure and a second image of the second set of instructions to be conducted by the surgical scrub during the second step of the surgical procedure.

20 Claims, 13 Drawing Sheets

Surgery-HMMC
HMMC Pick List(HMMC IntraOp Record)

Procedure:      Toe Arthrodesis
Surgeon:
Specialty:      Podiatry
Pref Card Id:   9563070

| ITEM REPORTING CLASS<br>ITEM DESCRIPTION | ITEM NUMBER | OPEN QTY | HOLD QTY |
|---|---|---|---|
| DRESSINGS/SPONGES | | | |
| BANDAGE GAUZE CONFORM STRL 2 2231 | 100605 | 1 | 0 |
| DRESSING GAUZE XEROFORM 1X8 8884433301 | 101621 | 1 | 0 |
| GLOVES | | | |
| GLOVE SURGEON 7 1/2 5711104 | 100661 | 1 | 0 |
| GLOVE SURGEON PROTGRTY 7 5NT 2D72N570 | 155388 | 1 | 0 |
| IMMOBILIZERS | | | |
| SHOE POSTOP FEM LG 2044-09 | 100418 | 0 | 1 |
| SHOE POSTOP FEM MED 2044-08 | 100419 | 0 | 0 |
| INSTRUMENTS | | | |
| CUTTER PIN SMALL | EQ1151 | 0 | 0 |
| HANDLE LIGHT NEW | EQ1342 | 1 | 0 |
| POWER DRILL MINI DRIVER 3-M | EQ1192 | 0 | 1 |
| SAW MICRO-SAGGITAL | EQ1585 | 1 | 0 |
| SET PODIATRY | EQ1767 | 1 | 0 |
| MEDS | | | |
| BACITRACIN VIAL 50,000 UNITS FOR IRRIG | RX0057 | 0 | 1 |
| BUPIVACAINE 0.25% 30ML MPF (MARCAINE/SENSORCAINE) | RX0079 | 0 | 1 |
| CEFAZOLIN 1GM VIAL (ANCEF/KEFZOL) | RX0099 | 2 | 0 |
| POLYMYXIN B 500,000 UNITS VIAL | RX0486 | 0 | 1 |
| SODIUM CHLORIDE 0.9% 1500ML IRRIG (BOTTLE) | RX0651 | 1 | 0 |
| VANCOMYCIN 1 GM VIAL FOR CEMENT ADD | RX0633 | 1 | 0 |
| PACKS/DRAPES | | | |
| PACK GOWN SURGICAL XLG 1/PK 9040 | 101721 | 1 | 0 |
| PACK ORTHO MAJOR CUSTOM | 150920 | 1 | 0 |
| STOCKINETTE IMPERVIOUS MED 1586 | 101903 | 1 | 0 |
| PANS/BASINS | | | |
| BASIN SETS METAL | EQ1013 | 1 | 0 |
| STERILE SUPPLIES | | | |
| BLADE SAW SAG 9.5X25.5 KM-101 | 115812 | 1 | 0 |
| BLADE SURGICAL 10 371110 | 100624 | 2 | 0 |
| BLADE SURGICAL 15 371115 | 100621 | 4 | 0 |
| CAUTERY PENCIL E-Z CLEAN 0030E | 158399 | 1 | 0 |
| COVER TOURNIQUET LG 53605 | 106898 | 1 | 0 |
| GOWNS CLOTH | R1001 | 2 | 0 |
| SCALPEL DISP W/ SLEEVE 15 2315-N-SMI | 159970 | 0 | 1 |
| SET PINS K-WIRE STEINMAN PLAIN | EQ1453 | 0 | 1 |
| TOWELS 4/PACK | R1000 | 2 | 0 |
| SUTURES | | | |
| SUT ETHILON 3-0 18 PS2 1669H | 110119 | 1 | 0 |
| SUT PROLENE 4-0 18 PS2 8682G | 109563 | 1 | 0 |
| SUT VICRYL 2-0 27 SH J417H | 112141 | 1 | 0 |
| SUT VICRYL 3-0 27 SH J416H | 113143 | 1 | 0 |
| SUT VICRYL 4-0 18 PS2 J496H | 109595 | 1 | 0 |
| UNSTERILE EQUIPMENT | | | |
| HOSE NITROGEN BLACK | EQ1397 | 1 | 0 |
| MACHINE CAUTERY VALLEY LAB | EQ1082 | 1 | 0 |
| MACHINE TOURNIQUET NON-DIGITAL | EQ1384 | 1 | 0 |

Printed: 03/29/2005 13:41:00

Fig. 2A
*(PRIOR ART)*

HMMC Pick List(HMMC IntraOp Record)Continued

Procedure: Toe Arthrodesis
Surgeon:
Specialty: Podiatry
Pref Card Id: 9565070

| ITEM REPORTING CLASS ITEM DESCRIPTION | ITEM NUMBER | OPEN QTY | HOLD QTY |
|---|---|---|---|
| TOURNIQUET SINGLE VALVE/CUFF ALL SIZES | 301886 | 1 | 0 |

Procedure Specific Preference Card Comments:
    Preference Card Comments
        Circulators:
        Circulator:
        Askabout DAB and Marcaine
        Have x-rays in room if available         Position: Supine         Prep:
        Prep foot to ankle with Iodophor         Dressing:
        Xeroform 1 x 8

3" Kling
        4" Ace General Provider Comments:
<None>
Procedure Specific PickList Comments:
<None>

Printed: 03/29/2005 13:41:00    Page 2

Fig. 2B
*(PRIOR ART)*

```
Resource Map
GYHYSABDTO, HYSTERECTOMY, ABDOMINAL ,TOTAL
in SURGERY HMSW
Surgeon:
IntraOperative
        HSW - SURGEON GLOVE SIZE
            7-1/2 REGULAR                           ─ 21
        HSW - ASSIST GLOVE SIZE
            RICKY TEKELL, RN    GLOVE: 7-1/2 ORTHO
        HSW - HINTS
            SUCTION AND CAUTERY OFF PATIENT'S LEFT SHOULDER
            INSERT FOLEY WITH VAG PREP
            USE POPOFF VICRYL FOR SUTURE PASSERS
            NO ELECTRIC HAIR CLIPPERS OR MASTISOL
            MAKE SURE VICRYL CONTROL RELEASE SUTURE IS NO MORE THAN
            18" LONG
        HSW - POSITION
            SUPINE, ARMS ON BILATERAL BOARDS
        HSW - PREP
            BETADINE SCRUB AND PAINT, VAG & ABD
        HSW - MEDICATIONS -- IRRIGATIONS
            NACL IRRIG X 2 (1 IN KIT) (WARM)

MARCAINE 0.25% W/EPI
        HSW - CAUTERY SETTINGS
            COAG -- 35    CUT: 60
        HSW - SUTURE/BLADE
            USE POPOFF VICRYL FOR SUTURE PASSERS

MAKE SURE VICRYL CONTROL RELEASE SUTURE IS NO MORE THAN 18" LONG -- DO NOT USE
            J741  27"
        HSW - DRESSING
            TELFA -- IN KIT
            FLATS -- IN KIT
            ABD
            3" MEDIPORE TAPE
            PERI PAD -- IN KIT
            CHUX TO PACU BED -- IN KIT

Page 1 of 2
                                                            Print Date/Time:  7/19/2006  6:50:10PM
                                                            Report ID: casecardpract.rpt
                                                            Sub Report ID: resmapinstruct.rpt
```

Resource Map
GYHYSABDTO, HYSTERECTOMY, ABDOMINAL ,TOTAL
In SURGERY HMSW
Surgeon:

IntraOperative
HSW - LEVEL CHARGE

| Item Mfr.Cat.No. | Description | Open UM | Hold L/T | Used Wstd |
|---|---|---|---|---|
| 300082110 | OR LV V | 0 EA | 0 | |

HSW - ANESTHESIA CHARGES

| Item Mfr.Cat.No. | Description | Open UM | Hold L/T | Used Wstd |
|---|---|---|---|---|
| 302060070HSV | DESFLURANE | 0 EA | 0 | |
| 302060056HSV | GENERAL 1ST HOUR | 0 EA | 0 | |
| 302060057HSV | GENERAL EACH ADDL 30 MINUTES | 0 EA | 0 | |
| 302060066HSV | ISOFLURANE | 0 EA | 0 | |
| 302060060HSV | MAC 1ST HOUR | 0 EA | 0 | |
| 302060061HSV | MAC EACH ADDL 30 MINUTES | 0 EA | 0 | |
| 302060062HSV | REGIONAL / SPINAL 1ST HOUR | 0 EA | 0 | |
| 302060063HSV | REGIONAL/ SPINAL EACH ADDL 30 MINUTES | 0 EA | 0 | |
| 302060069HSV | SEVOFLURANE | 0 EA | 0 | |

HSW - SURGEON GLOVE SIZE

| Item Mfr.Cat.No. | Description | Open UM | Hold L/T | Used Wstd |
|---|---|---|---|---|
| 998476621HSV 2D7254 | GLOVE SURG REGULAR 7.5 | 1 EA | 0 L/ | |

HSW - ASSIST GLOVE SIZE

| Item Mfr.Cat.No. | Description | Open UM | Hold L/T | Used Wstd |
|---|---|---|---|---|
| 998476672HSV 2D7284 | GLOVE SURG ORTHOPEDIC 7.5 | 1 EA | 0 L/ | |

HSW - EQUIPMENT

| Item Mfr.Cat.No. | Description | Open UM | Hold L/T | Used Wstd |
|---|---|---|---|---|
| E-CAUTERY-S | CAUTERY,ESU,VALLEY LAB | 1 EA | 0 | |
| E-SUCTION-S | SUCTION | 1 EA | 0 | |

HSW - MEDICATIONS – IRRIGATIONS

| Item Mfr.Cat.No. | Description | Open UM | Hold L/T | Used Wstd |
|---|---|---|---|---|
| M-NACL-IR-1L | NACL IRRIG 1000 ML BOTTLE | 1 EA | 0 | |

HSW - SUPPLIES & SOFT GOODS

| Item Mfr.Cat.No. | Description | Open UM | Hold L/T | Used Wstd |
|---|---|---|---|---|
| 304510016HSV 65651-530 | LINER CANNISTER SUCTION 3000CC | 0 EA | 1 | |
| 998255027HSV PB41HYHSR | PACK ABDONMINAL HYSTERECTOMY PBDS KIT | 1 EA | 0 L/ | |
| S-TOWELS4P | TOWELS, 4 PACK | 1 EA | 0 | |

HSW - INSTRUMENTS

| Item Mfr.Cat.No. | Description | Open UM | Hold L/T | Used Wstd |
|---|---|---|---|---|
| T-GYN-SW | GYN TRAY | 1 EA | 0 | |
| I-HEANBAL-ST | HEANEY BALLENTINE CLAMPS-STRAIGHT | 2 EA | 0 | |
| T-MAJOR-SW | MAJOR TRAY | 1 EA | 0 | |
| I-ROGER-ST-S | ROGERS HYSTERECTOMY CLAMP, STRAIGHT | 2 EA | 0 | |
| I-SCHNIDTZ-S | SCHNIDTZ CLAMPS | 2 EA | 0 | |

HSW - SUTURE/BLADE

| Item Mfr.Cat.No. | Description | Open UM | Hold L/T | Used Wstd |
|---|---|---|---|---|
| 998473011HSV 73-8010 | BLADE SCALPEL SAFETY CARTRIDGE #10 PERSONNA | 1 EA | 0 L/ | |
| 998471368HSV 811H | SUTR CHROMIC 2-0 CT-1 27" 811H | 1 EA | 0 | |
| 998471264HSV J946H | SUTR VICRYL 0 CT-1 36" UNDYED J946H | 3 EA | 0 L/ | |
| 998471217HSV J840D | SUTR VICRYL 0 CT-1 CR-8 18" UNDYED J840D | 2 EA | 0 L/ | |
| 998471396HSV J944H | SUTR VICRYL 3-0 CT-1 36" UNDYED J944H | 1 EA | 0 L/ | |

HSW - PYXIS - MEDICATIONS

| Item Mfr.Cat.No. | Description | Open UM | Hold L/T | Used Wstd |
|---|---|---|---|---|

Page 2 of 3
Print Date/Time: 7/19/2006 6:50:10PM
Report ID: casecardpract.rpt
Sub Report ID: resmapinstruct.rpt

Fig. 3B
*(PRIOR ART)*

Resource Map
GYHYSABDTO, HYSTERECTOMY, ABDOMINAL ,TOTAL
In SURGERY HMSW
Surgeon:
M-BU-0.25%W, BUPIVACAINE (MARCAINE) 0.25%  1   0
    W/EPI 30 ML
                                           EA

HSW - PYXIS – OR'S

| Item #<br>Mfr Cat No. | Description | Open<br>UM | Hold<br>L/T | Used<br>Wstd |
|---|---|---|---|---|
| 998715638HSV<br>7196 | ABD PAD | 1<br>EA | 0<br>L/ | |
| 304672770HSV<br>PMW35 | SKIN STAPLER PMW-35 (WIDE) | 1<br>EA | 0<br>L/ | |

← 19

Page 3 of 3
Print Date/Time: 7/19/2006 6:50:10PM
Report ID: casecardpract.rpt
Sub Report ID: resmapinstruct.rpt
Sub Report ID: resmapitem.rpt

Doctor XXXX XXXX M.D.
XL Gown, Size 7 Perry Gloves

Assistant, CFA
XL Gown, Size 7½ Biogel Gloves

• Confirm: SMALL or LARGE
  Oconnor-Osullivan retractor

• Ask about On-Q Pain Pump ― 51

Incision & Exposure

2 Lap sponges — dry

10 Blade — on #3 Knife handle

Cooley scissors — transect Rectus Abdominus facia

Crile hemostat

Cooley scissors — open Peritoneum

Doctor XXXX XXXX M.D.

Total Abdominal Hysterectomy

→ Drape & Setup

4 Cloth towels - no clips

Transverse Laparatomy Sheet

Light Handles & Cautery Pencil

Suction tube & Poole tip (guard removed)

VIRTUAL SURGICAL ASSISTANT

CROSS REFERENCE TO RELATED APPLICATIONS

This application is a Continuation-in-part of U.S. application Ser. No. 11/789,723, filed 24 Apr. 2007, titled "Virtual Surgical Assistant," which is hereby incorporated by reference for all purposes as if fully set forth herein.

BACKGROUND OF THE INVENTION

1. Field of the Invention

The present invention relates to systems for storing and presenting surgeon-specific, surgical-procedure guidelines and preferences to surgical team members preparing for, and in particular, assisting surgeons during, surgical procedures.

2. Description of Related Art

It takes many people working together as a team to perform a surgical operation. The primary surgeon leads the team and is responsible for the safe and competent performance of the operation. Additional team members will depend upon the type of surgery, the precise procedures, and the primary surgeon's preferences. The team may include other doctors, advanced practice nurses, physician assistants, registered nurses, surgical technicians, manufacturer representatives, and other medical specialty personnel. The additional team members have specific supporting roles, are responsible for particular tasks, and strive to perform them as proficiently and accurately as possible.

Surgical facility personnel are normally responsible for obtaining, organizing, and preparing the necessary instruments, tools, equipment, and supplies required and preferred by individual surgeons to perform a surgical procedure. Although many surgical procedures require a certain basic set of instruments, most surgical procedures require certain specialized instruments, subject to surgeon preference regarding type, brand, style, and preparation for use. Preparation of an operating room for a surgical procedure involves appropriate positioning and set-up of furniture and equipment, which may be mandated by surgeon preference.

The surgical scrub, normally a nurse or technician, is the team member responsible for arranging and organizing the sterile instruments and supplies on one or more sterile tables and trays in preparation for a surgical procedure. Following proper patient positioning on the operating room table and appropriate surgical site preparation, the surgical scrub assists in draping the patient, according to surgeon preference, and creating a sterile field around the surgical site. Sterile cords and tubes required to connect sterile implements, such as electrosurgical and suction devices, to unsterile equipment are placed and secured to the sterile field according to surgeon preference and passed off the sterile field for connection.

Once the operation has begun, it is the job of the surgical scrub to pass the instruments, tools, and supplies to the surgeons at the appropriate time during the surgical procedure or when requested by the surgeons. The slightest mistake or delay by the surgical scrub in handling or passing an instrument to the surgeon can cause the surgeon to lose concentration and become frustrated with the surgical scrub. Thus, it is necessary that the surgical scrub not only be familiar with each step of the operation so that she will be ready with the next instrument to be used, but be familiar with the individual preferences of each surgeon and individual preferences of the first assistant if included as a team member. Individual preferences are often finely differentiated. For example, some surgeons prefer certain suture needles placed on a needleholder at the middle of the needle and at an angle of 90°, while other surgeons prefer the same suture needle used for the same purpose placed on the needleholder ⅔ from the tip at an angle of 60°. Current methods require surgical scrub personnel to memorize and recall the individual preferences of multiple surgeons and first assistants for multiple surgical procedures, skills that can only be achieved by surgical scrub personnel through extensive experience.

Over the years, various methods have been developed to assist surgical staff members in preparation for surgical procedures. One method is to manually prepare individual "preference cards" for each surgical procedure that a surgeon performs. These preference cards list the surgeon's name, the name of the surgical procedure, and the standard instrument sets or trays, equipment, and supplies that the surgeon prefers. Preference cards typically include personal preferences, such as the size and type of glove that the surgeon prefers, preferences for specific sutures and needles, and preferences for specific additional instruments not included in the standard sets or trays.

Figure 1A:
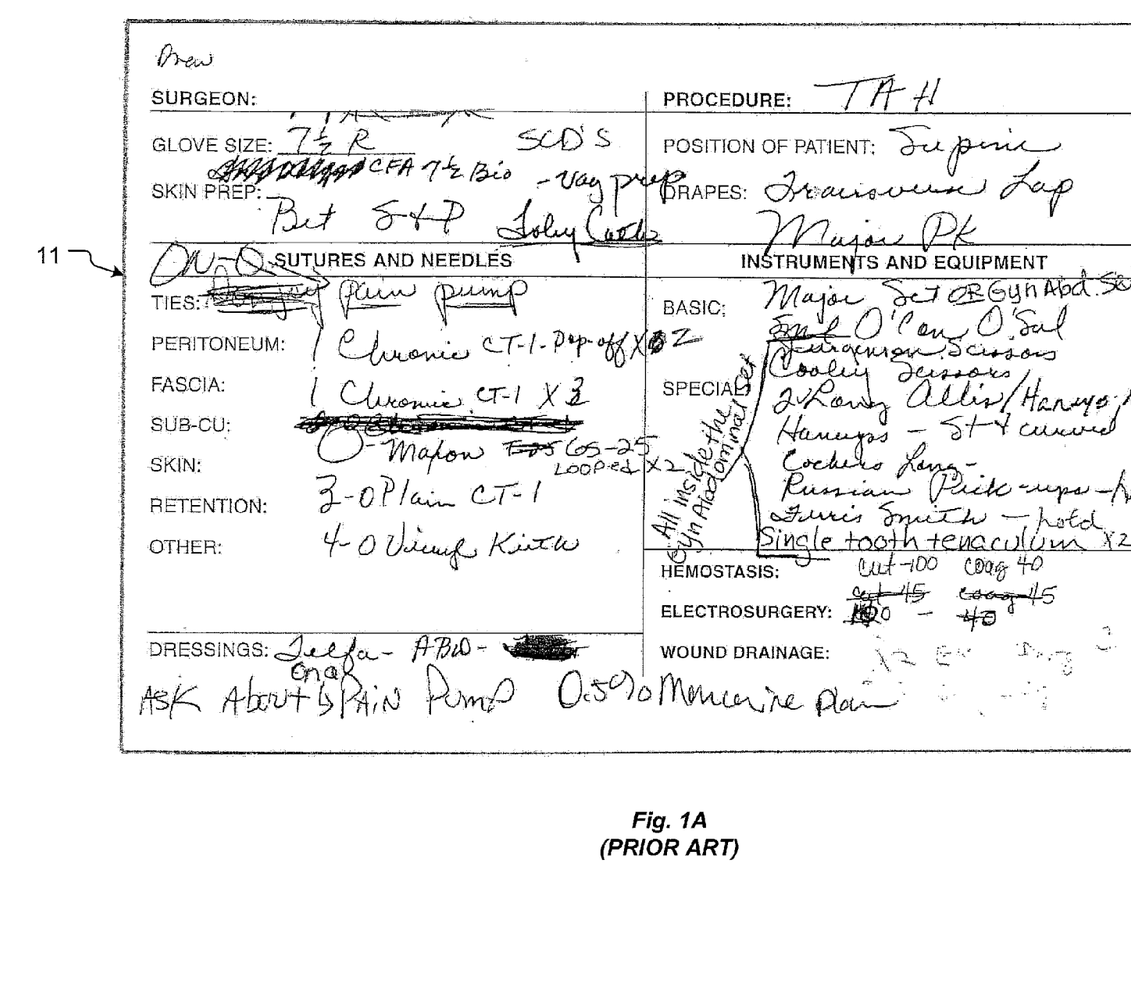
FIGS. 1A and 1B are the front and back sides, respectively, of a typical two-sided prior-art preference card for a particular surgeon and a particular surgical procedure.
Figure 1B:
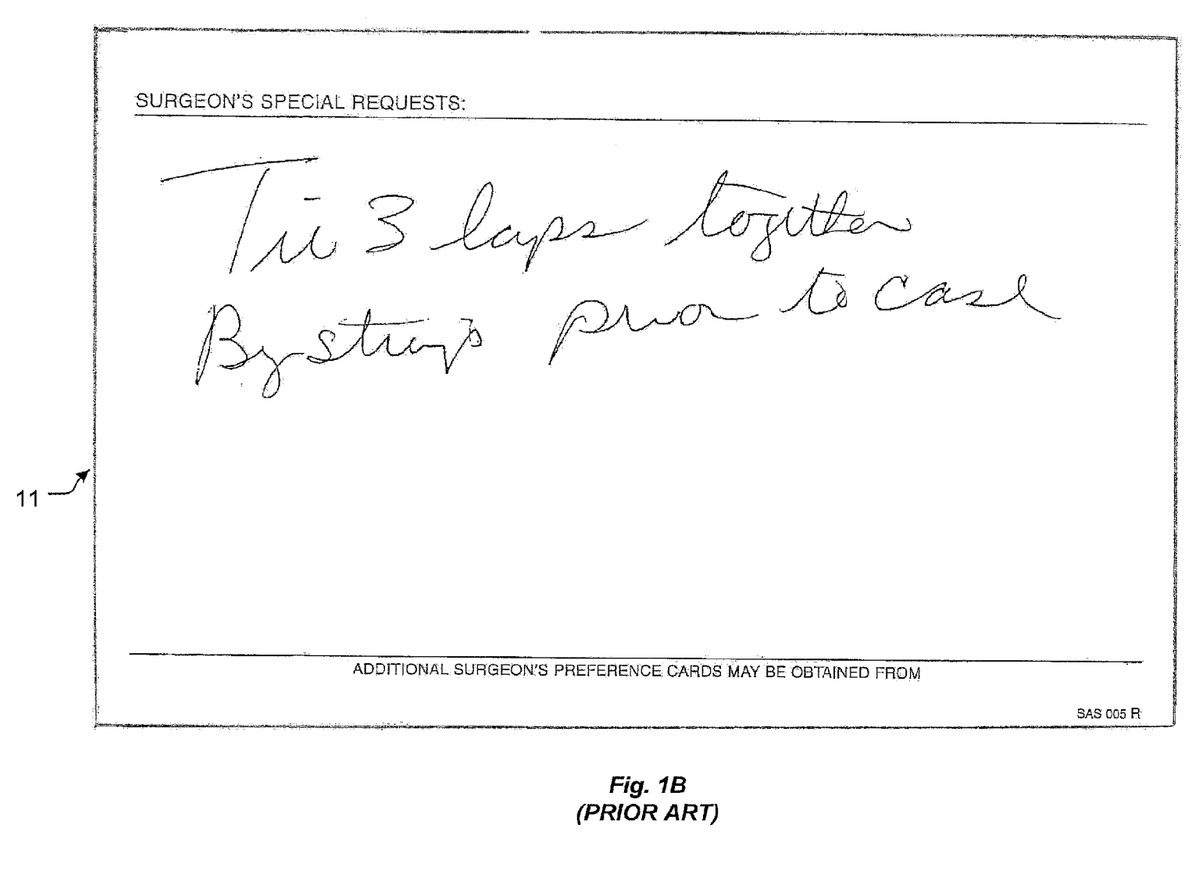

One such preference card 11 is illustrated in FIGS. 1A and 1B. As shown, preference card 11 is basically a form printed on an index-type card that has been filled out and updated manually by the facility staff. With this method, a separate preference card must be prepared and updated for each different surgeon and for each different surgical procedure that the surgeon performs. This is time consuming and susceptible to duplication errors. Because preference card 11 is maintained and updated manually by hand, preference card 11 is often messy, with scratch-outs and writing in the margins and on the back side. This makes preference card 11 difficult to read, which can lead to mistakes being made by the surgical facility staff when preparing for the surgical procedure.

Although preference cards are still in use today, many hospitals and surgical centers have implemented more advanced systems to be used by surgical facility staff in preparing for surgical procedures. For example, many hospitals and surgical centers now have computerized databases called "pick lists" that contain all of the instruments and supplies that are required for a particular surgical procedure. Pick lists are generally more detailed than preference cards and contain more specific information, such as part numbers for the instruments, and whether certain sterile packages should be opened prior to the surgical procedure or remain unopened but readily available.

Figure 2B:
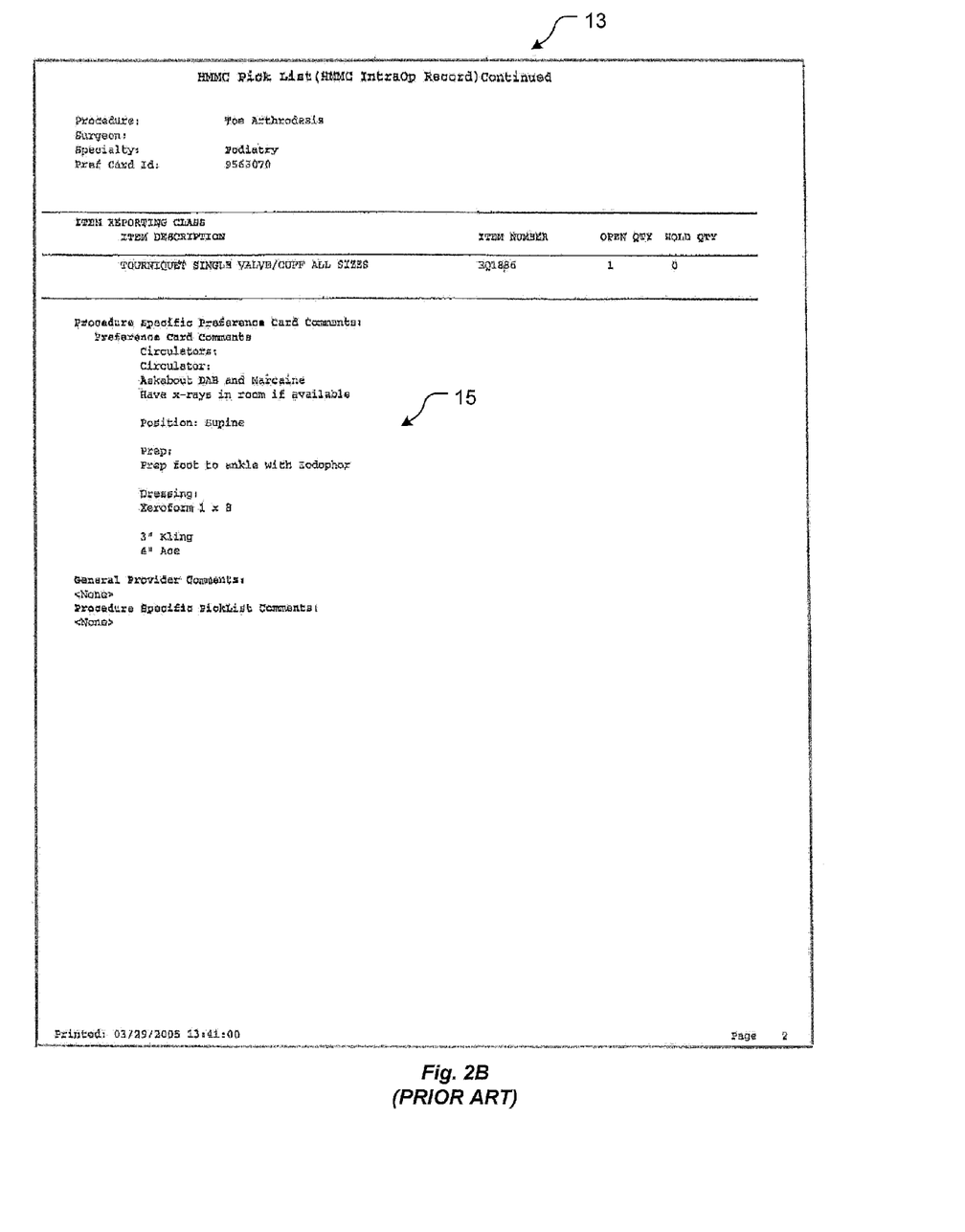

One such pick list 13 is shown in FIGS. 2A and 2B. Pick list 13 provides details on which instruments and materials the surgeon will need and the state of readiness for each item. Thus, pick list 13 is useful for gathering the instruments, tools, and materials that will be used during the surgical procedure, but provides little assistance once the surgical procedure has begun. Pick list 13 may include a "comments" section, such as section 15, which might include some surgeon-specific preferences.

Figure 3A:
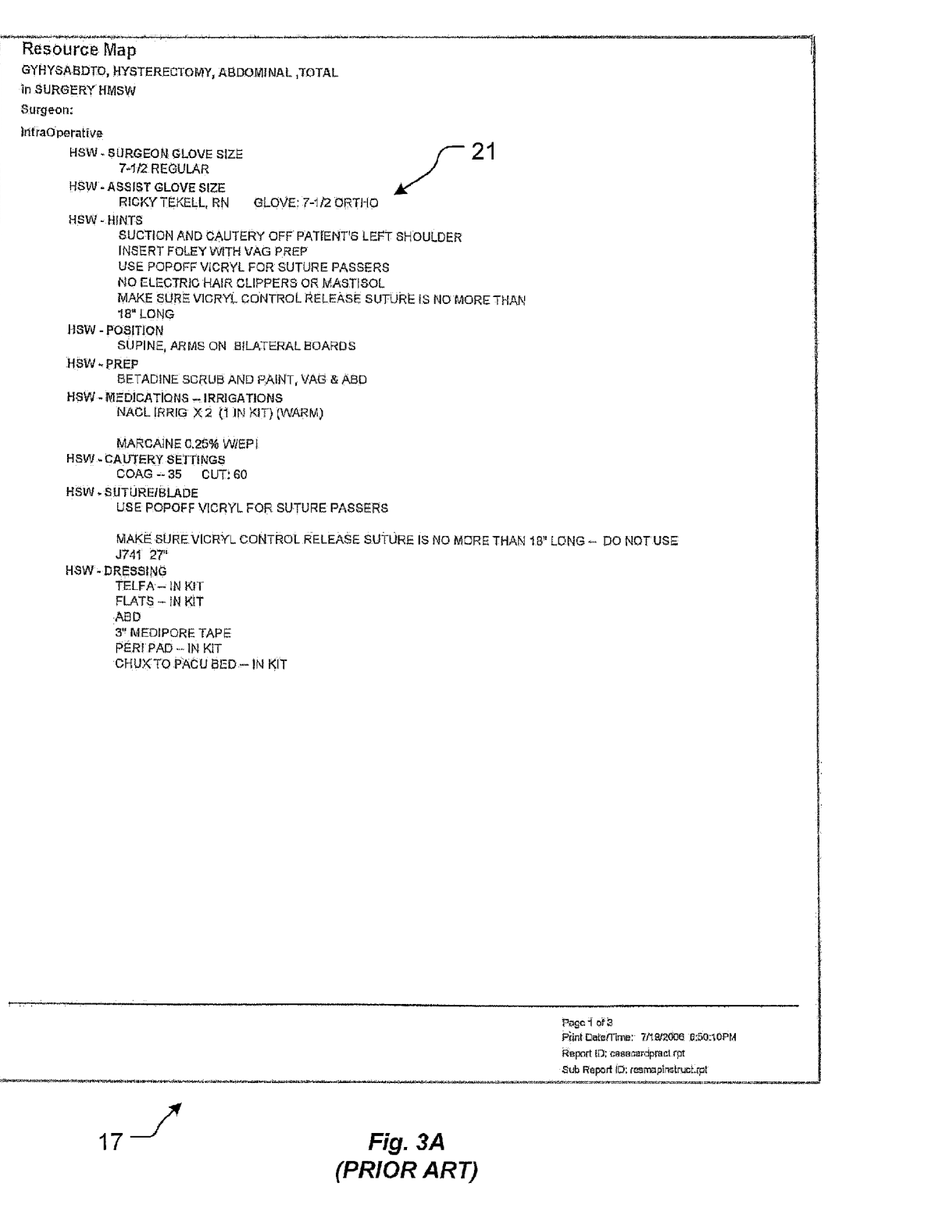
Figure 3C:
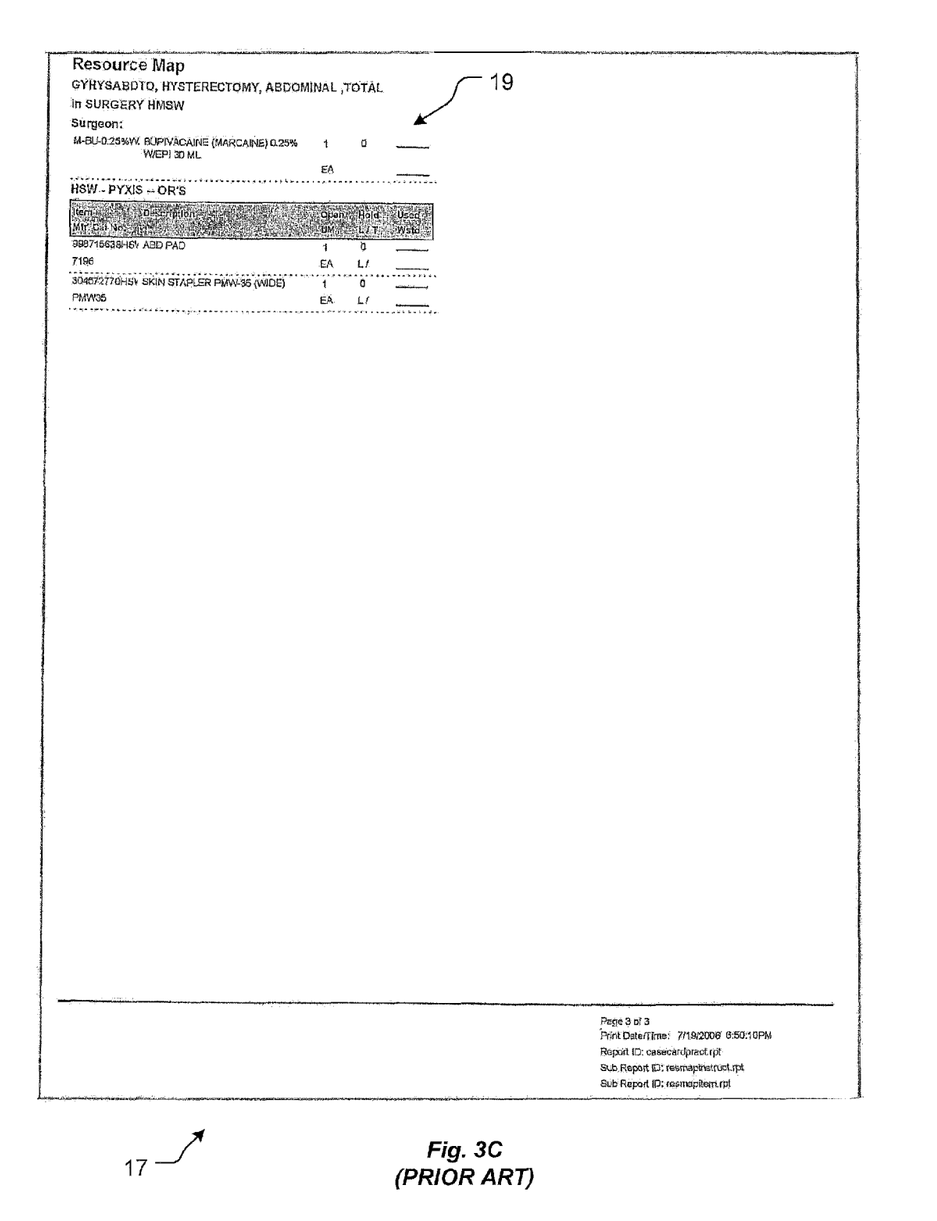

Another device used by hospitals and surgical centers in preparation for surgical procedures is a "resource map." Resource maps are very similar to pick lists, with the exception that resource maps are more detailed and include fields to capture data on how many items on the list were actually used and how many were wasted. One such resource map 17 is shown in FIGS. 3A-3C. As is shown, resource map 17 is similar to pick list 13, with the exception that resource map 17 includes a column 19 to record which items were used and which were not used, or wasted. As with pick list 13, resource map 17 may include a section 21 that sets forth some surgeon-specific hints or preferences.

The significant drawback to preference cards, pick lists, and resource maps is that none of these devices are available to, or of practical use during, the actual surgical procedure by the surgical-scrub team member after donning a sterile surgical gown and gloves. In addition, none of these devices list the instruments, tools, and materials in the order of use during the surgical procedure. These preference cards, pick lists, and resource maps are arranged and organized by categories of supplies and instruments. For example, the different sutures are all listed together, the different instruments are listed together, the medicines are all listed together, etc. This makes sense, because preference cards, pick lists, and resource maps are designed to help surgical facility staff gather the supplies that will be needed for an operation, and these supplies are usually stored together in a supply room. These devices are not designed for use by the surgical scrub during an operation. The intra-operative surgeon-specific hints or preference information these devices contain must be studied and memorized by the surgical scrub prior to the surgical procedure.

Aside from preference cards, pick lists and resource maps, hospitals and surgical centers have developed other types of systems for use in conjunction with surgical services. These other developments include standardized surgical kits and complicated enterprise-wide systems designed to track inventory and costs associated with entire surgical departments.

All of the systems and devices described above are useful in preparing for a surgical procedure and some are designed to provide inventory management information. All of the systems and devices described above have the significant drawback of not providing the surgical scrub with intra-operative surgeon's preference guidance for a given surgical procedure. In addition, none of the systems or devices described above list the order in which particular instruments and tools will be used by a particular surgeon performing a particular surgical procedure. Furthermore, these devices and systems do not include any type of graphical representation of the instruments or how the instruments may be organized in the surgical theater. None of the systems or devices described above are designed to be used by the surgical scrub during the actual surgical procedure.

Therefore, while there have been significant developments in the area of surgical facility and procedure information systems, considerable shortcomings remain.

BRIEF DESCRIPTION OF THE DRAWINGS

The novel features believed characteristic of the invention are set forth in the appended claims. However, the invention itself, as well as, a preferred mode of use, and further objectives and advantages thereof, will best be understood by reference to the following detailed description when read in conjunction with the accompanying drawings, wherein:

FIGS. 2A and 2B are the first and second pages, respectively, of a typical two-page prior-art pick list for a particular surgeon and a particular surgical procedure;

FIGS. 3A, 3B, and 3C are the first through third pages, respectively of a typical prior-art three-page resource map for a particular surgeon and a particular surgical procedure;

DETAILED DESCRIPTION

There is a need for an automated system that can be used by surgical support team members to assist in pre-operative organization and intra-operative management of surgical instruments, tools, supplies, and equipment. The system of the present application is an automated system that can be used by surgical support team members, including sterilely gowned and gloved surgical scrub personnel, as a surgeon-specific, surgical-procedure guide to pre-operative organization and intra-operative management of surgical instruments, tools, supplies, and equipment.

This is achieved by providing a virtual surgical assistant system that is located in the operating theater for use by supporting surgical team members, including sterilely gowned and gloved surgical scrub personnel. The system comprises a computer, a display, a remotely operable input device, and a presentation hosted on the computer that represents a chronological, step-by-step guide to a surgical procedure as performed by a specific surgeon.

The system provides significant advantages, including: (1) providing valuable information to the surgical support team members; (2) increasing the amount of accessible information available to the surgical scrub team member without compromising sterility; (3) providing the surgical scrub live information about surgeon-specific procedure routines and preferences; (4) facilitating surgical scrub anticipation of and efficient response to surgeon requests; (5) allowing a surgical scrub to work competently for different surgeons or on different procedures with little or no experience; (6) allowing surgical facilities to provide surgeons with more consistent levels of surgical scrub service. Additional objectives, features, and advantages will be apparent in the written description that follows.

The system and method of the present application will be understood, both as to its structure and operation, from the accompanying drawings, taken in conjunction with the accompanying description. Several embodiments of the assembly are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that features, elements, and/or functions of one embodiment may be incorporated into another embodiment as appropriate, unless described otherwise.

The present application provides an automated system that can be used during a surgical operation to assist surgical scrub personnel in the preparation and handling of surgical equipment, instruments, tools, and materials. For simplification purposes, the term "instrument" will be used herein to identify various equipment, instruments, tools, material, and other supplies used in connection with a surgical procedure. In the preferred embodiment, the system is located in the operating theater for use by surgical facility surgical support team members, and comprises a computer system, a display system, at least one input device, and a presentation software program hosted on the computer system and displayed on the display system. In the preferred embodiment, the computer system is a desktop computer, the display system is a large computer monitor, the input device is a wireless mouse, and the presentation is a textual and graphical software program representing a chronological, step-by-step outline of a specific surgical procedure as routinely performed by a specific surgeon. The system is also referred to herein as a "virtual surgical assistant."

The system includes one or more databases that store data related to particular surgical procedures and particular surgeons, including certain surgeon-specific preferences that may not be available on existing preference cards, pick lists, and resource maps. The system can be customized for each surgeon and each surgical procedure. Although the system of the present application will be described herein with respect to a stand-alone computer system, it will be appreciated that the present application may also be carried out over computer networks of various sizes and configurations. Indeed, certain data and components of the system may be stored and carried out in remote locations over various computer and telecommunications networks, including the Internet and wireless networks. For example, some of the software and databases of the system may be stored on separate computer networks of the hospital or surgical center. In another example, a central data processing computer system may be used that allows "virtual surgical assistant" data to be shared throughout an entire city, country, or around the world.

In the preferred embodiment, the input device is a wireless mouse operably associated with the desktop computer. The wireless mouse is carried in a pouch that is worn around the neck of surgical scrub personnel underneath the surgical gown, or otherwise carried on the person of or in the clothing of the surgical scrub. This ensures that the mouse does not adversely effect the sterility of the operating theater. The wireless mouse communicates with the desktop computer in a manner that does not adversely affect the electronics, wireless communications, and telecommunications used by any equipment in the operating theater. In the preferred embodiment, the wireless mouse communicates with the desktop computer via an RF (radio frequency) connection. In some applications it may be desirable to have the wireless mouse communicate with the laptop via encrypted communication system, such as the Bluetooth communication system. By wearing the wireless mouse around his neck or in close proximity to his person, the surgical scrub can quickly and easily manipulate and control the system without being distracted from her duties during the operation.

It will be appreciated that other input devices may be equally suitable. For example, a foot pedal input device may be used. Some input devices are wired, others use infrared communication, others use a radio standard. The choice of input device will be dictated by the surgical environment and other equipment being used within the operating theater. In some cases, it may be desirable to use a wired input device, so as to reduce the possibility of interference with other equipment and to increase durability. For example, where other wireless equipment is in use, or in remote locations with limited technical support, such as military surgical units, a wired input device would have certain advantages. Likewise, where mobility is important and additional wires are to be avoided, a wireless input device might be preferred. In addition, in some applications, it may be desirable to have a back-up input device available should the primary input device fail or lose battery power.

The system may include a variety of graphical user interfaces and different modes of operation. For example, one interface may be used for initial data entry, and other interfaces may be used for maintenance, updating, and reporting. In the preferred embodiment, a slideshow-type graphical user interface is used by the surgical scrub during an operation. In this "operation mode," only one slide at a time is displayed on the display. Each slide includes various text, graphics, and color coordinated schemes that represent and emphasize the different stages of the operation and the individual instruments that are required during that stage. For example, different colors, schemes, and/or interfaces may be used to emphasize different stages of an operation, or may be used to emphasize selected instruments or steps in procedure.

The virtual surgical assistant allows the surgical scrub to step through the operation in a chronological sequence. As each step of the operation is completed, the surgical scrub clicks an appropriate button on the mouse, thereby causing the presentation to advance and display the next slide on the display, or in those embodiments in which multiple displays are used, to advance the presentation across the multiple displays. Each slide provides surgeon specific surgical procedure and preference information to the surgical scrub prompting anticipation and preparation of surgical instruments routinely used for the next step of the procedure. In some applications, the surgical scrub may chose between different levels of detail being presented on the slides. For example, some surgical scrubs may be very familiar with certain surgeons or certain procedures, and may choose to use a very low level of detail in the slides. In other instances, the surgical scrub may not be familiar with a particular procedure and may wish to use an interface that provides a high level of detail on each slide. These choices between interfaces and modes may be quickly and easily made by the surgical scrub at any time.

With the virtual surgical assistant of the present application, the surgical scrub has immediate access to all pertinent information related to the instruments required for the operation, as well as, all surgeon-specific preferences. This allows the surgical scrub to be better prepared for the operation and to better anticipate the needs of the surgeons.

Referring now to FIGS. 4A-4J in the drawings, an exemplary slideshow for a particular surgical procedure according to the preferred embodiment of the present application is illustrated. Each of FIGS. 4A-4J corresponds to a separate slide 31-49, respectively. In the preferred embodiment, the surgical procedure is separated into separate chronological stages, with each stage having one or more steps or instructions set forth on one or more slides. Each slide lists instruments and/or surgeon-specific preferences that are needed during the chronologically corresponding portion of the surgical procedure.

Figure 4A:
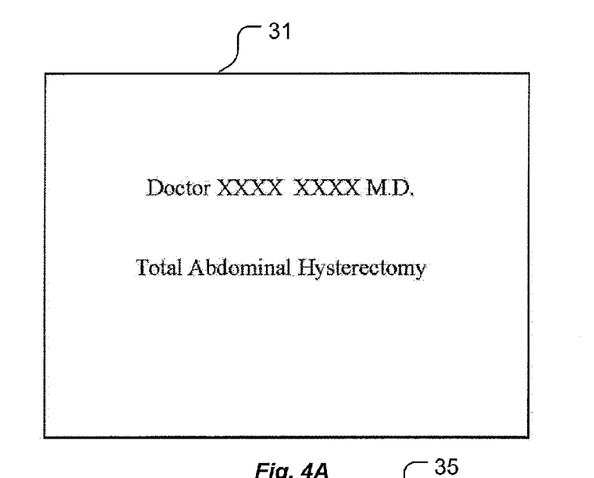
FIGS. 4A-4J are thumbnail views of slides of an exemplary slideshow for a particular surgical procedure for a particular surgeon in accordance with the preferred embodiment of the virtual surgical assistant system of the present invention.
Figure 4B:
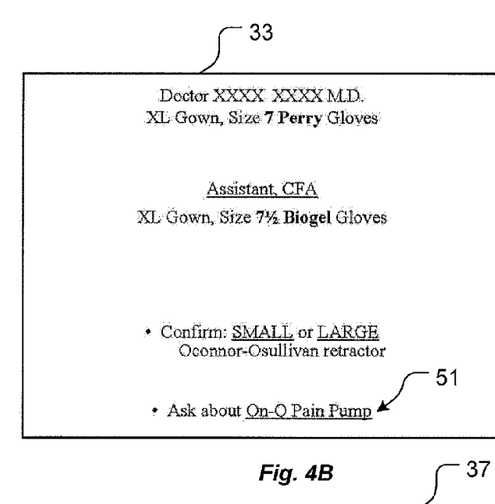
Figure 4C:
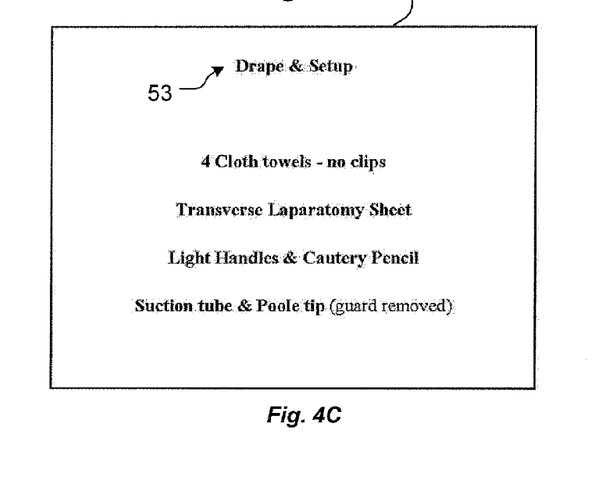

As shown in slide 31 of FIG. 4A, the surgical procedure of this example is a total abdominal hysterectomy being performed by the specific Doctor. In slide 33 of FIG. 4B, some surgeon-specific data is displayed, including the preferred glove type and size for the lead surgeon and her assistant surgeon. As is shown at instruction 51, the surgical scrub is instructed to inquire about the "On-Q Pain Pump." Continuing with slide 35 in FIG. 4C, a surgical stage indicator 53 serves as a heading for the steps of the "Drape and Setup" stage. It will be appreciated that certain stage indicators and certain procedures may be color coded or otherwise highlighted or emphasized to accentuate different levels of importance or detail. The Drape and Setup slide may include certain surgeon-specific preferences as to how the surgeon prefers the drapes to be arranged on the patient and how the surgeon prefers the instruments to be configured.

Figure 4D:
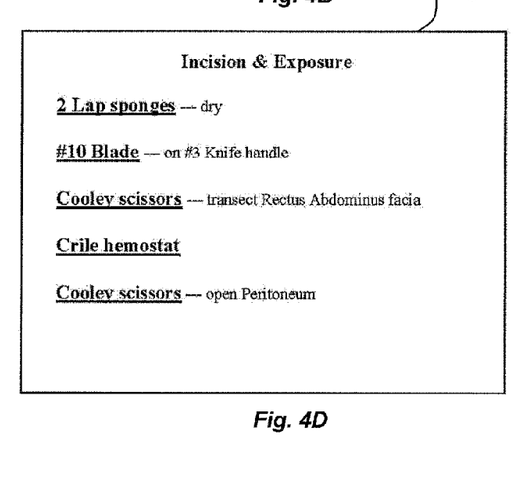
Figure 4E:
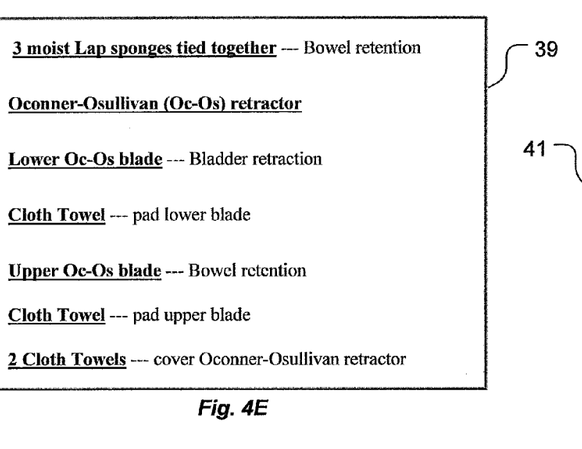
Figure 4F:
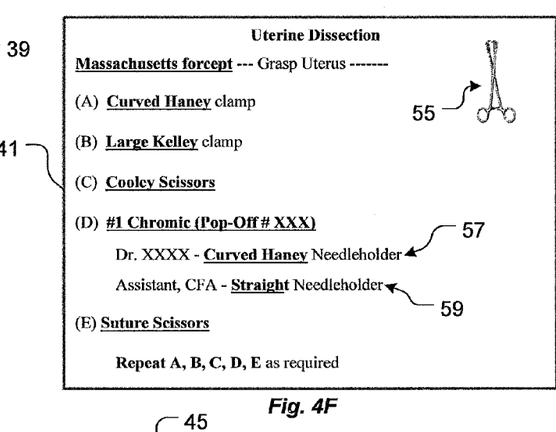
Figure 4G:
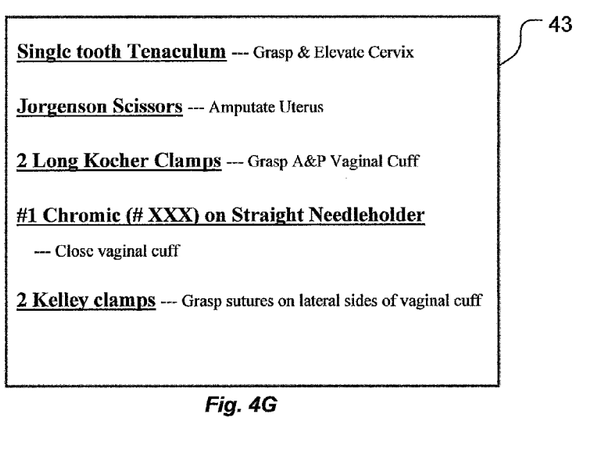
Figure 4H:
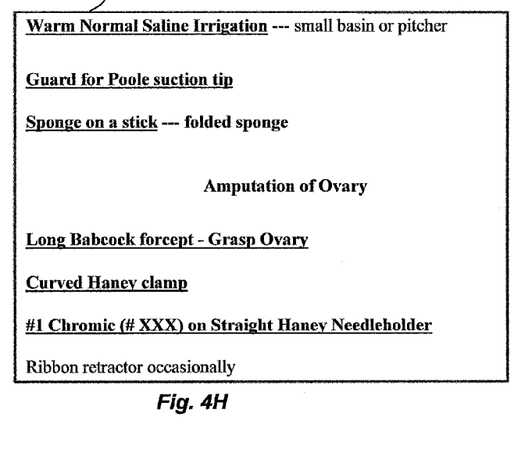
Figure 4I:
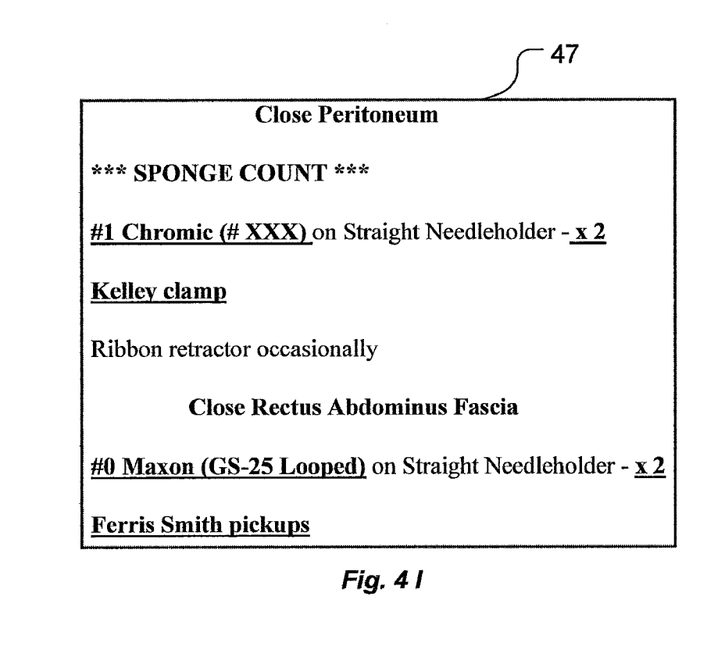
Figure 4J:
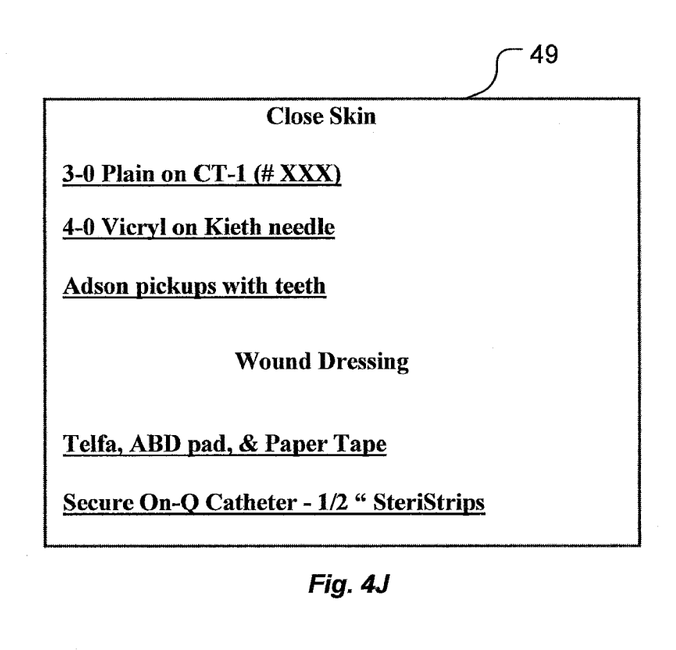

Slides 37 and 39 of FIGS. 4D and 4E set forth the steps and instruments needed during an "Incision & Exposure" stage. Next, in slides 41-45 of FIGS. 4F-4H, the steps and instruments needed during a "Uterine Dissection" stage are presented. As is shown, slide 41 includes a graphical picture 55 of a curved Haney clamp. Graphics and pictures, such as picture 55, are particularly helpful to surgical scrubs in situations where the instruments are not well known, not frequently used, or are easily confused with other instruments. Also shown in FIG. 4F are two surgeon-specific preferences 57 and 59. Preferences 57 and 59 denote the types of needle holders that the surgeon and her assistant prefer. Slide 41 might also include a picture of the exact way that the surgeon prefers to have the suture needle be clamped to the suture clamp. This information saves time during the operation, because the surgeon does not have to stop and reconfigure the suture needle in the clamp. The remaining stages of the operation are set forth on slides 45-49 of FIGS. 4H-4J, respectively.

Figure 5A:
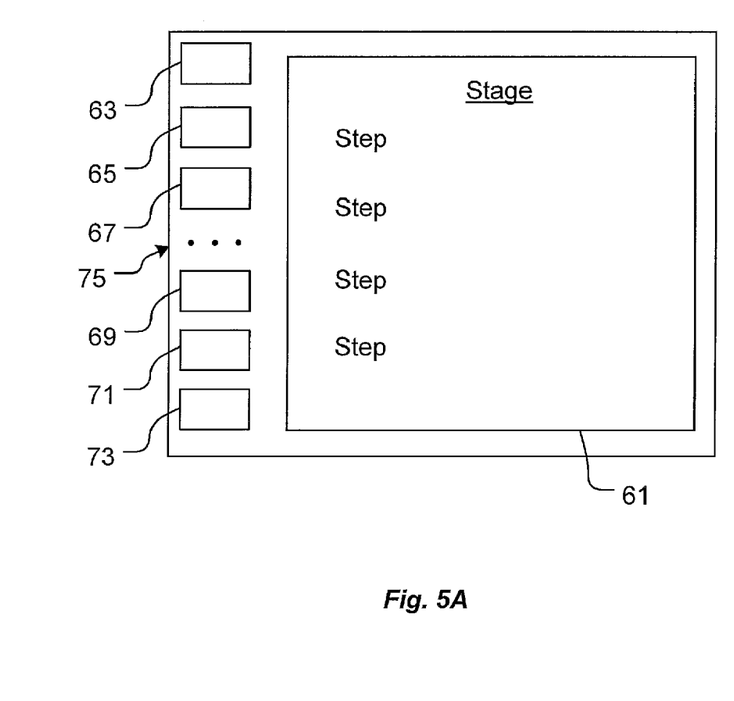
FIGS. 5A and 5B are schematics of thumbnail views of slides having an alternate graphical user interface in accordance with an alternate embodiment of the virtual surgical assistant system of the present invention.
Figure 5B:
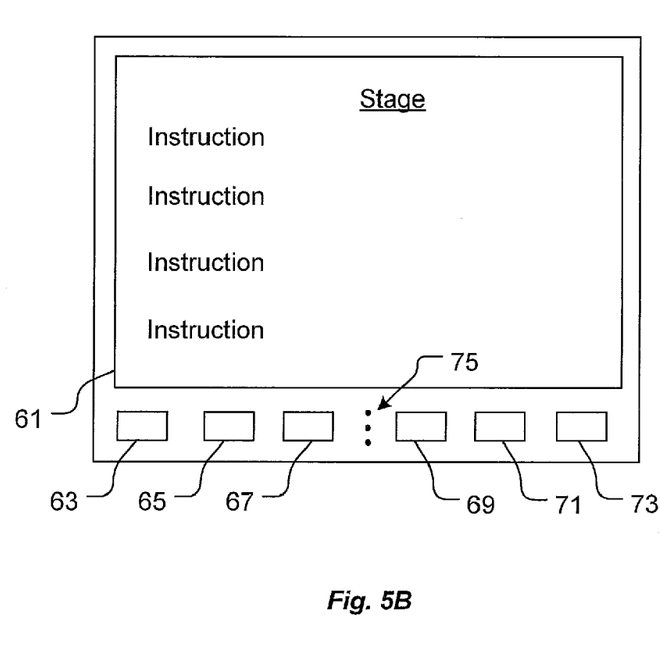

Referring now to FIGS. 5A and 5B in the drawings, alternate embodiments of the graphical user interface for the slideshow are illustrated. In the graphical user interfaces of FIGS. 5A and 5B, multiple slideshow screens are displayed on the display simultaneously. In FIG. 5A, a current slide 61 is shown occupying most of the display area. Slides 63, 65, and 67 are show in reduced size, i.e., a thumbnail size, and represent slides that have already been completed, while slides 69, 71, and 73 are also shown in reduced size and represent slides displaying upcoming steps. A textual or graphic indicator 75 may be used as a placeholder for current slide 61. FIG. 5B illustrates a similar interface with the thumbnail images of completed and upcoming slides arranged along the bottom of the display area. It will be appreciated that a wide variety of graphical user interfaces may be used depending upon the application and the personal choice of the surgical scrub using the system. It should be understood that the hardware and software of the virtual surgical assistant system of the present application may be adapted to support multiple display monitors. For example, a multiple slides can be displayed in a "full screen" mode across multiple monitors. This allows the information in the slides to be display at an optimum size. In such an embodiment, it would be preferred that the slides progress from one monitor to the next.

Figure 6:
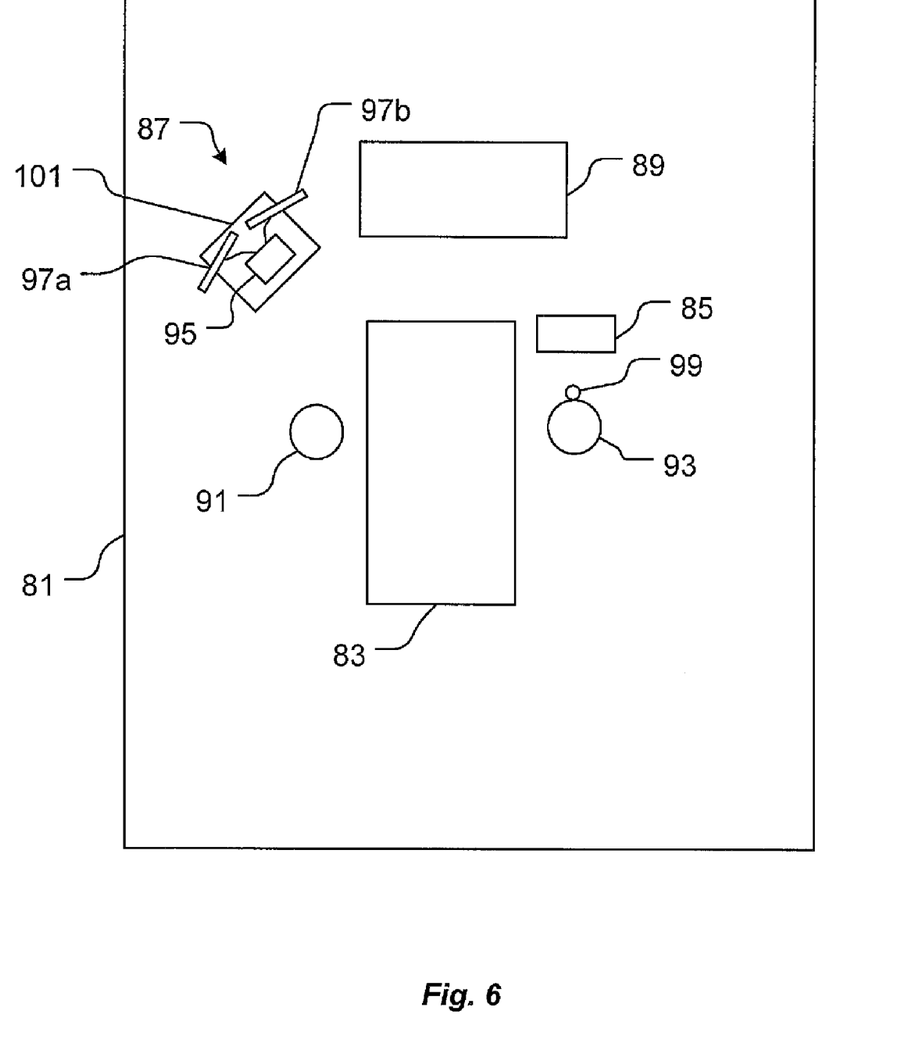
FIG. 6 is a plan view of a surgical theater having a virtual surgical assistant system according to the present invention.

Referring now to FIG. 6 in the drawings, a plan view of a surgical theater 81 having a virtual surgical assistant according to the present application is illustrated. Surgical theater 81 includes a primary operating table 83, a mayo tray 85, a virtual surgical assistant system 87, and a variety of conventional surgical equipment 89. In this exemplary layout, a surgeon 91 is positioned on one side of operating table 83, and a surgical scrub 93 is positioned on the other side of operating table 83 next to mayo tray 85. Mayo tray 85 contains a wide assortment of surgical instruments, tools, materials, and medicine. Mayo tray 85 has been prepared prior to the operation according to instructions on a slideshow stored on virtual surgical assistant system 87. The set-up slides of the slideshow might show a graphical representation of Mayo tray 85 and include a surgeon-specific preference that a certain location on Mayo tray 85 be left open for surgeon 91 to place used instruments.

Virtual surgical assistant system 87 comprises a laptop (or desktop) computer 95, one or more display monitors 97a and 97b, and a wireless mouse 99 carried in a person thereon or the clothing of surgical scrub 93 under the sterile gown of surgical scrub 93. In this example, computer 95 and display monitors 97a and 97b are stand-alone units carried on a support structure, such as a cart or stand 101. It will be appreciated that the support structure may be a cart, table, stand, rack, or other type of frame that is used by other equipment in the operating theater. By utilizing support members that are used for other purposes in the operating theater, the limited space in the operating theater can be optimized. It should be understood that virtual surgical assistant system 87 may reside, run, and be displayed over multiple computer systems, including but not limited, to the hospital displays already provided in the operating room. This is particularly useful when the operating theater is crowded with other equipment 87.

During the operation, surgical scrub 93 passes instruments to and from Mayo tray 85 and to and from surgeon 91 as necessary or as requested. As the operation progresses, surgical scrub 93 clicks the appropriate buttons on mouse 99 to advance the slideshow through the different stages of the operation. Throughout the operation, the slideshow is available for viewing by surgical scrub 93. This allows surgical scrub 93 to anticipate the upcoming moves of surgeon 91, resulting in a very proficient and accurate procedure.

Figure 7:
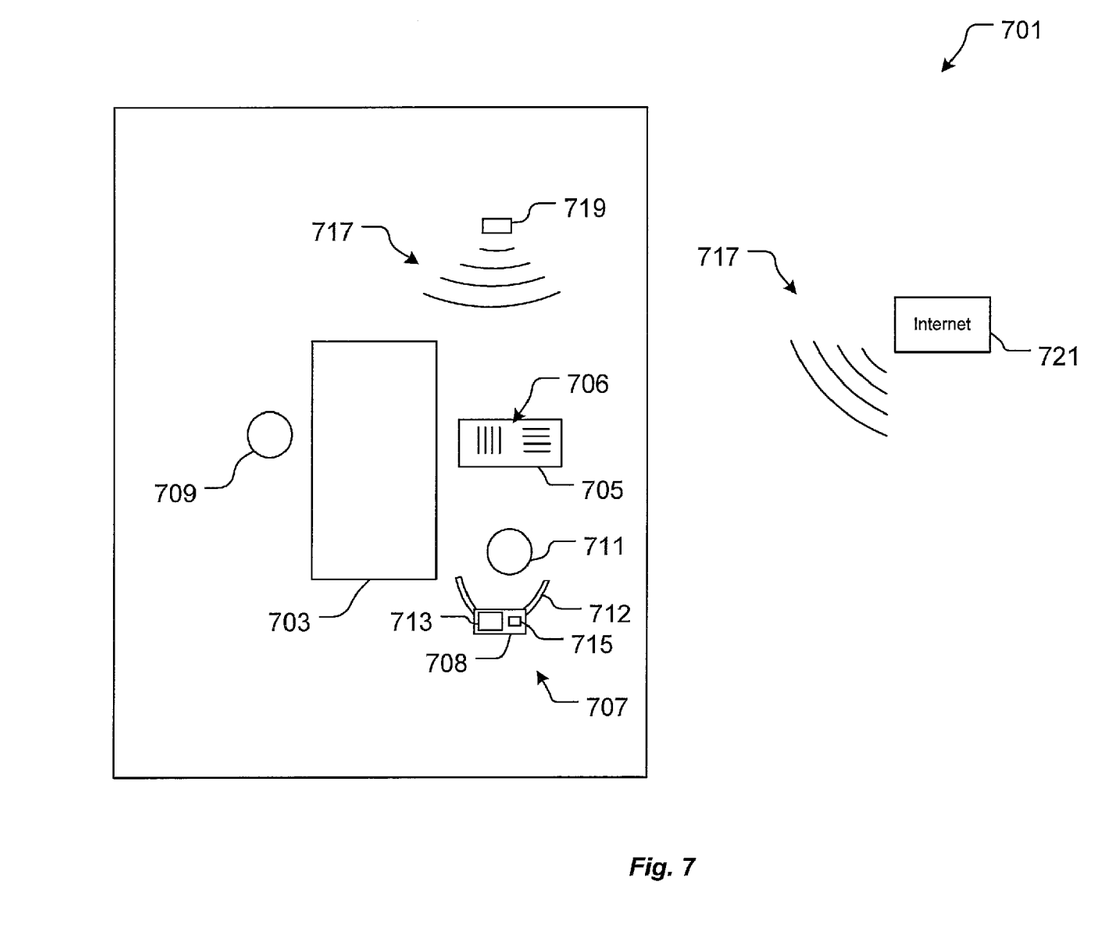
FIG. 7 is a plan view of an alternative embodiment of the surgical theater of FIG. 6.

Referring next to FIG. 7 in the drawings, a plan view of an alternative embodiment of surgical theater 81 is shown. Surgical theater 701 is substantially similar in function to surgical theater 81, and it will be appreciated that one or more of the features of surgical theater 81 discussed herein are incorporated in theatre 701. Likewise, the features of theatre 701 could easily be incorporated in theatre 81 in an alternative embodiment of the present application.

Surgical theater 701 preferably includes one or more of a primary operating table 703, a mayo tray 705, and a virtual surgical assistant system 707. During operation, a surgeon 709 is positioned on one side of operating table 703, while a surgical scrub 711 is positioned on the opposing side of the table 703 next to mayo tray 705. It should be understood that mayo tray 705 is utilized to carry a wide assortment of surgical instruments, tools, materials, and medicine 706 for use during the operation. These instructions are provided to the surgical scrub 711 via the virtual surgical assistant system 707.

It will be appreciated that system 707 is configured to provide step-by-step instructions to the surgical scrub 711 of pre-determined procedural steps from surgeon 709. It should be understood that each surgeon 709 includes a preferred method of treatment, thus requires different tools and equipment to be utilized in selective order. System 707 provides effective means for informing scrub 711 of the surgeon's procedural requests. Further description of system 707 is provided below.

In this exemplary embodiment, system 707 is a portable device 708 which can be configured to attach directly onto surgical scrub 711 via an attachment means 712, e.g., a strap securely attached thereto, or placed nearby. In the preferred embodiment, device 708 is a smartphone, tablet, touchpad, heads-up device, or other suitable means for displaying the surgeon's instructions, e.g., request for tools during the procedure. System 707 comprises an interactive display 713 for displaying the surgeon's instructions, and could optionally be provided with a wireless receiver 715 for receiving and transmitting data 717 to and from either a remote computer 719 and/or the world-wide web internet 721. It should be understood that computer 719, internet 721, and/or device 708 utilizes a database having a program that stores step-by-step instructions from the surgeon. In some embodiments, the program stored within the database could be part of an enterprise software system, for example, a hospital software system utilized by the entire facility. It should also be realized that computer 719 is easily adapted to include internet access. As discussed above, the program is pre-programmed with instructions from the surgeon such as which tools to use during a specific step in the operation.

In one embodiment, interactive display 713 is configured to be interactively manipulated, e.g., with a finger or voice control, wherein the surgical scrub can easily toggle between different slides of instructions. Alternative embodiments could include wireless devices, such as a wireless mouse, operably associated with the database for manipulating instructions displayed on display 713.

During operation, surgical scrub 711 passes instruments to and from Mayo tray 705 and to and from surgeon 709 as necessary or as requested. As the operation progresses, surgical scrub 711 toggles between different instructions to advance the program to the next set of instructions. Throughout the operation, the instructions are available for viewing by surgical scrub 711. This allows surgical scrub 711 to anticipate the upcoming operation moves of surgeon 709, resulting in a very proficient and accurate procedure.

It is apparent that a system and method with significant advantages has been described and illustrated. Although the system and method have been shown in a limited number of forms, they are not limited to just these forms, but are amenable to various changes and modifications without departing from the spirit thereof.

I claim:

1. A proactive surgical assistant system for use by a surgical scrub during a surgical procedure conducted by a surgeon, the surgical assistant system comprising:
   a portable device having:
      a display; and
   a database in data communication with the portable device, the database having:
      a program having:
         a first image of a first pre-selected items to be used by the surgeon during a first step of the surgical procedure; and
         a second image of a second pre-selected item to be used by the surgeon during a second step of the surgical procedure;
   wherein the display displays the first image and the second image; and
   wherein the surgical scrub manipulates the portable device for viewing the first image during the first surgical step, then to the second image during the second surgical step.

2. The system of claim 1, the portable device further comprising:
   a wireless receiver in data communication with the database;
   wherein the database wirelessly transmits the first image and the second image to the portable device via the wireless receiver.

3. The system of claim 2, wherein the database is a world-wide web internet system.

4. The system of claim 2, wherein the database is a remote computer located remotely from an operating theater in which the surgical procedure is taking place.

5. The system of claim 1, wherein the portable device is a smartphone.

6. The system of claim 5, further comprising:
   a wristband for securing the smartphone to the surgical scrub.

7. The system of claim 1, wherein the portable device is a tablet.

8. The system of claim 1, wherein the program is a slideshow program in which a chronological listing of instructions is displayed on the display in a plurality of sequential slides.

9. The system of claim 8, wherein the chronological listing of instructions is specific to one surgeon and one procedure.

10. The system of claim 1, wherein the display includes a plurality of displays.

11. A proactive surgical assistant system for use by a surgical scrub during a surgical procedure conducted by a surgeon, the surgical assistant system comprising:
    a portable device carried on the surgical scrub, the portable device having:
       a display; and
    a database in data communication with the portable device, the database having:
       a program having:
          a first slide having a first image of a first pre-selected instructions to be carried out by surgical scrub during a first step of the surgical procedure; and
          a second slide having a second image of a second pre-selected instructions to be carried out by the surgical scrub during a second step of the surgical procedure;
    wherein the display displays the first instructions and the second instructions; and
    wherein the surgical scrub manipulates the portable device between the first instructions during the first surgical procedure, and then to the second instructions as the surgeon transitions from the first step to the second step of the surgical procedure.

12. The system of claim 11, the portable device further comprising:
    a wireless receiver in data communication with the database;
    wherein the database wirelessly transmits the first slide and the second slide to the portable device via the wireless receiver.

13. The system of claim 12, wherein the database is a world-wide web internet system.

14. The system of claim 12, wherein the database is a remote computer located remotely from an operating theater in which the surgical procedure is taking place.

15. The system of claim 11, wherein the portable device is a smartphone.

16. The system of claim 15, further comprising:
    a wristband for securing the smartphone to the surgical scrub.

17. The system of claim 11, wherein the first instructions and the second instructions include textual data and graphical images of selected surgical items.

18. A proactive method of assisting a surgeon during a surgical procedure, the method comprising:
    pre-selecting and storing a first image of a first instructions from the surgeon in a database prior to the surgical procedure;
    pre-selecting and storing a second image of a second instructions from the surgeon in the database prior to the surgical procedure;
    transmitting the first image and the second image from the database to a portable device;
    displaying on a display of the portable device the first image;
    conducting the first instructions during a first surgical step of the surgical procedure based upon the display of the first image;
    advancing to the second image after the first surgical step;
    displaying on the display the second image; and conducting the second instructions during the second surgical step of the surgical procedure based upon the display of the second image.

19. The method of claim 18, wherein the process of transmitting the first image and the second image to the portable device is achieved wirelessly through a wireless receiver.

20. The method of claim 18, further comprising:
securing the portable device to a surgical scrub assisting the surgeon during the surgical procedure with a strap attached to the portable device.

* * * * *